United States Patent [19]

Adam

[11] Patent Number: 4,785,096
[45] Date of Patent: Nov. 15, 1988

[54] PROCESS FOR THE PREPARATION OF 1,4-DIAMINO-2,3-DICYANOANTHRAQUINONES

[75] Inventor: Jean-Marie Adam, Rosenau, France

[73] Assignee: Ciba-Geigy Corporation, Ardsley, N.Y.

[21] Appl. No.: 145,024

[22] Filed: Jan. 19, 1988

Related U.S. Application Data

[62] Division of Ser. No. 26,084, Mar. 16, 1987, Pat. No. 4,738,800.

[30] Foreign Application Priority Data

Mar. 26, 1986 [CH] Switzerland .................. 1206/86

[51] Int. Cl.$^4$ .................. C07C 97/24; C07D 223/26
[52] U.S. Cl. .................. 544/69; 260/378; 558/289
[58] Field of Search .................. 544/69; 558/289; 260/378

[56] References Cited

U.S. PATENT DOCUMENTS

| | | | |
|---|---|---|---|
| 2,496,414 | 2/1950 | Seymour et al. | 260/378 |
| 2,800,472 | 7/1957 | Schwechter et al. | 260/378 |
| 3,140,313 | 7/1964 | Kitasaki et al. | 558/289 |
| 3,621,023 | 11/1971 | Padmanabhan | 558/189 |
| 4,042,605 | 8/1977 | Hartwig | 260/378 |
| 4,299,769 | 10/1981 | Kröck et al. | 260/378 |
| 4,299,771 | 11/1981 | Takeshita et al. | 260/378 |
| 4,422,973 | 12/1983 | Kröck et al. | 260/378 |
| 4,659,817 | 4/1987 | Gallop et al. | 558/289 |
| 4,661,292 | 4/1987 | Schanlin et al. | 260/378 |

Primary Examiner—Richard L. Raymond
Assistant Examiner—Raymond Covington
Attorney, Agent, or Firm—Kevin T. Mansfield; Edward McC. Roberts

[57] ABSTRACT

There is disclosed a process for the preparation of 1,4-diamino-2,3-dicyanoanthraquinones by reacting compounds of formula

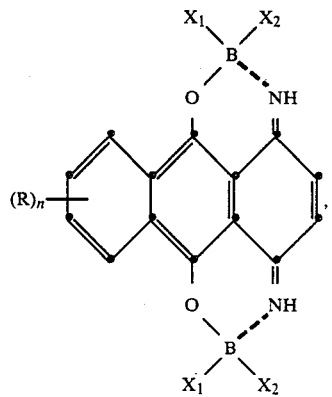

wherein $X_1$ and $X_2$ are hydroxyl, halogen, acetate or sulfato ester, or, when taken together, are an oxygen atom attached by a double bond to the boron atom, R is a substituent and n is 0, 1 or 2, with an inorganic cyanide in a polar aprotic solvent and in the presence of an oxidizing agent, and subsequently hydrolyzing the reaction product.

5 Claims, No Drawings

PROCESS FOR THE PREPARATION OF 1,4-DIAMINO-2,3-DICYANOANTHRAQUINONES

This is a divisional of application Ser. No. 026,084 filed on Mar. 16, 1987, now U.S. Pat. No. 4,738,800.

The present invention relates to a novel process for the preparation of 1,4-diamino-2,3-dicyanoanthraquinones.

A number of processes for the preparation of 1,4-diamino-2,3-dicyanoanthraquinone, which is an important intermediate for dye synthesis, are known to the literature. Thus, for example, a process in which 1,4-diaminoanthraquinone, or a derivative thereof which is substituted in 2- and/or 3-position by chlorine or bromine, is reacted with a cyanide, is disclosed in German Offenlegungsschrift No. 24 24 748.

In view of the great importance of 1,4-diamino-2,3-cyanoanthraquinone, this process affords the desired product in too low a yield and purity.

Hence it is the object of the present invention to provide a novel process by means of which 1,4-diamino-2,3-dicyanoanthraquinones can be obtained in higher yield and greater purity than heretofore.

It has now been found that the cyanation of the anthraquinone system in 2- and 3-position can be carried out in simple manner after converting, 1,4-diaminothraquinones into boron complexes having a 1,4-quinonediimine structure.

Accordingly, the present invention relates to a process for the preparation of 1,4-diamino-2,3-dicyanoanthraquinone, which comprises reacting a boron complex of formula

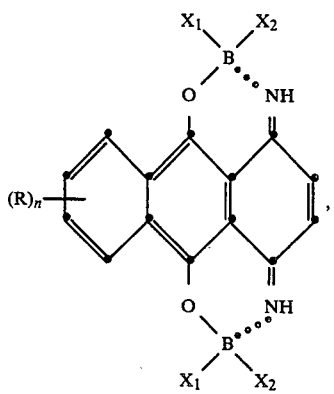

(1)

wherein $X_1$ and $X_2$ are each hydroxyl, halogen, acetate or sulfato ester, or, when taken together, are an oxygen atom attached by a double bond to the boron atom, R is a substituent and n is 0, 1 or 2, with an inorganic cyanide in a polar aprotic solvent and in the presence of an oxidising agent, hydrolysing the reaction product so obtained and isolating the resultant 1,4-diamino-2,3-dicyanoanthraquinone.

The invention further relates to the novel boron complexes of formula (1), wherein $X_1$ and $X_2$ are halogen, to a process for the preparation of said complexes, and to the compounds obtainable by the processes of the invention.

In the boron complexes of formula (1), $X_1$ and $X_2$ are halogen, acetate or sulfate. Preferably $X_1$ and $X_2$ are fluorine, chlorine or bromine, with fluorine being particularly preferred.

R may be selected from a great number of substituents that do not interfere with the process of the invention. Preferred substituents R are alkyl, alkoxy, —CO$_2$alkyl and —CONHalkyl, the alkyl and alkoxy moieties of which preferably contain 1 to 6 carbon atoms. R can also be an acid group such as —SO$_3$M and —CO$_2$M, wherein M is normally hydrogen, ammonium or an alkali metal atom, e.g. sodium or potassium. However, R may also be an electronegative group such as nitro, cyano or halogen, preferably chlorine or bromine.

The boron complexes of formula (1) can contain up to 2 substituents R. Accordingly, n is 0, 1 or 2. Unsubstituted boron complexes (n=0) are normally most preferred.

The reaction of the boron complexes with inorganic cyanides is carried out in a polar aprotic solvent. Examples of suitable solvents are dimethylsulfoxide, N,N-dimethylformamide, N-methylformamide, N-methylacetamide, formamide, acetamide, N-methylpyrrolidone, 2-pyrrolidone, N-formylmorpholine, N-formylpiperidine, pyridine, or mixtures of such solvents. Preferred solvents are N,N-dimethylformamide, N-methylformamide, 2-pyrrolidone, or mixtures thereof. Especially good results are obtained with 2-pyrrolidone.

Suitable inorganic cyanides are sodium, potassium and ammonium cyanide. It is preferred to use sodium cyanide.

The oxidising agent required for the cyanation of this invention is normally an organic nitro compound, (atmospheric) oxygen, dimethylsulfoxide or sulfur. Preferred contenders from the group of organic nitro compounds are nitrobenzene, dinitrobenzene and nitrobenzenesulfonic acid, with 3-nitrobenzenesulfonic acid being particularly preferred. Suitable oxidising agents are also metal oxides such as divanadium pentoxide.

If appropriate, the cyanation can also be carried out in the presence of ammonium salts, e.g. salts of ammonia as well as salts of primary, secondary and/or tertiary amines. Examples of suitable ammonium salts are ammonium chloride, ammonium sulfate, ammonium phosphate, ammonium acetate, methylammonium chloride, dimethylammonium chloride, trimethylammonium chloride and tetramethylammonium chloride, ethylammonium chloride, diethylammonium chloride, triethylammonium chloride and tetraethylammonium chloride, propylammonium chloride, butylammonium chloride, triethylbenzoylammonium chloride, as well as the corresponding sulfates and phosphates and mixtures of these salts.

The cyanation of this invention can be carried out in a wide temperature range. 1,4-Diamino-2,3-dicyanoanthraquinones are obtained in good purity and high yield after the hydrolysis by carrying out the process in the temperature range from 20° to 100° C., preferably from 60° to 100° C. and, most preferably, from 70° to 90° C.

The hydrolysis following the cyanation is preferably carried out at the boiling point of the reaction mixture. It can be advantageous to carry out the hydrolysis in the presence of a base, e.g. sodium hydroxide or potassium hydroxide, sodium carbonate or sodium bicarbonate, as a speeding up of the hydrolysis is often observed under such conditions.

A particularly preferred embodiment of the process of this invention comprises reacting a boron complex of formula

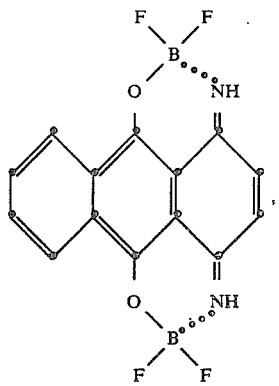

(2)

with sodium cyanide in 2-pyrrolidone and in the presence of 3-nitrobenzenesulfonic acid at 70° C. to 90° C., and, after addition of water, hydrolysing the reaction product so obtained under reflux.

It has been found advantageous to use, based on the boron complex, a 3- to 6-fold molar excess of organic cyanide, a 1- to 2-fold molar excess of oxidising agent, and a 5- to 10-fold amount (by weight) of solvent.

The 1,4-diamino-2,3-dicyanoanthraquinones are obtained by the above described process in high yield, usually from 70 to 80%, and in good purity, and can be used direct as intermediates for dye synthesis after being washed with e.g. water and without further purifying operations.

The novel boron complexes of formula (1) are prepared by reacting 1,4-diaminoanthraquinones with a boron trihalide, or with boron triacetate or boron trisulfate. It is preferred to use a boron trihalide, preferably in the form of an etherate such as $(C_2H_5)_2O.B(Hal)_3$. The use of $(C_2H_5)_2O.BF_3$ has proved especially advantageous.

The entire reaction is carried out in the temperature range from 120° to 170° C., preferably from 130° to 150° C., in an aromatic organic solvent which preferably contains halogen atoms, e.g. chlorobenzene, dichlorobenzene or trichlorobenzene. Dichlorobenzene, for example, has proved particularly suitable.

The boron complexes are obtained in high yield. After washing with the solvent employed, preferably in conjunction with benzene or toluene, they can be used for the preparation of 1,4-diamino-2,3-dicyanoanthraquinones.

The isolation of the boron complexes and of the 1,4-diamino-2,3-dicyanoanthraquinones is effected in conventional manner, e.g. by suction filtration or centrifugation, and subsequent washing and drying.

The invention is illustrated by the following non-limitative Examples.

EXAMPLE 1

Preparation of the compound of formula

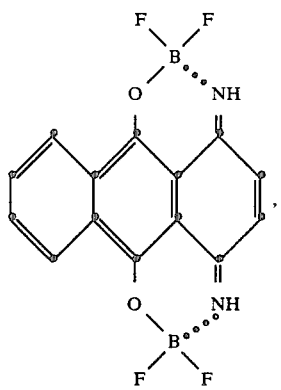

(2)

48 parts by weight of 1,4-diaminoanthraquinone are dissolved in 1000 parts by weight of o-dichlorobenzene at 160° C. and 114 parts by weight of boron trifluoride etherate are added. The reaction mixture is stirred for 10 hours at 140° C. and then filtered hot. The filter residue is washed with o-dichlorobenzene and toluene and dried.

Yield: 60 parts by weight of the compound of formula (2). The melting point is above 250° C.

| | Elemental analysis: $C_{14}H_8B_2F_4N_2O_2$ | | | | |
|---|---|---|---|---|---|
| | C | H | B | F | N |
| % theory | 50,4 | 2,4 | 6,5 | 22,8 | 8,4 |
| % found | 50,2 | 2,5 | 6,3 | 22,5 | 8,4 |

Carrying out the above procedure with 94 parts of boron trichloride or 200 parts of boron tribromide instead of with 114 parts of boron trifluoride etherate affords the corresponding bisboron chloride complex or bisboron bromide complex in comparably good yield.

EXAMPLE 2

Preparation of 1,4-diamino-2,3-dicyanoanthraquinone

A mixture of 41 parts by weight of sodium cyanide, 39 parts by weight of 3-nitrobenzenesulfonic acid (sodium salt) and 58 parts by weight of the compound of formula (2) is added in portions at 80° C. to 400 parts by weight of 2-pyrrolidone. The reaction mixture is stirred for 1 hour at 80° C., then diluted with 500 parts by weight of water and refluxed for 4 hours. The product precipitates in crystalline form during this hydrolysis. It is isolated hot by filtration, washed with water and dried.

Yield: 44 parts by weight of a product having a purity of 85% (analysis by HPLC), corresponding to a yield of 76%. The melting point is over 250° C.

Comparably good results are also obtained by replacing the bisboron fluoride complex of formula (2) by the corresponding bisboron bromide, bisboron acetate and bisboron sulfate complex.

EXAMPLE 3

Preparation of 1,4-diamino-2,3-dicyanoanthraquinone

A mixture of 41 parts by weight of sodium cyanide, 39 parts by weight of 3-nitrobenzenesulfonic acid (sodium salt) and 58 parts by weight of the compound of formula (2) is added in portions at 100° C. to 400 parts by weight of 2-pyrrolidone. The reaction mixture is stirred for 1 hour at 100° C., then diluted with 500 parts by weight of water and refluxed for 4 hours. The product precipitates in crystalline form during this hydrolysis. It is isolated hot by filtration, washed with water and dried.

Yield: 46 parts by weight of a product having a purity of 80% (analysis by HPLC), corresponding to a yield of 74%. The melting point is over 250° C.

Comparably good results are also obtained by using N-methylformamide, N,N-dimethylformamide, dimethylsulfoxide. N-methylacetamide or N-methylpyrrolidone instead of 2-pyrrolidone.

EXAMPLE 4

Preparation of 1,4-diamino-2,3-dicyanoanthraquinone

A mixture of 41 parts by weight of sodium cyanide, 13 parts by weight of dimethylsulfoxide and 58 parts by weight of the compound of formula (2) is added in portions at 60° C. to 400 parts by weight of 2-pyrrolidone. The reaction mixture is stirred for 4 hours at 60° C., then diluted with 500 parts by weight of water and refluxed for 4 hours. The product precipitates in crystalline form during this hydrolysis. It is isolated hot by filtration, washed with water and dried.

Yield: 40 parts by weight of a product havng a purity of 90% (analysis by HPLC), corresponding to a yield of 73%. The melting point is over 250° C.

Comparably good results are obtained by introducing air instead of using dimethylsulfoxide.

EXAMPLE 5

The procedure of Example 2 is repeated, using 40 parts by weight of 1,4-diaminoanthraquinone instead of 58 parts by weight of the compound of formula (2). No reaction is observed.

What is claimed is:
1. A compound of formula

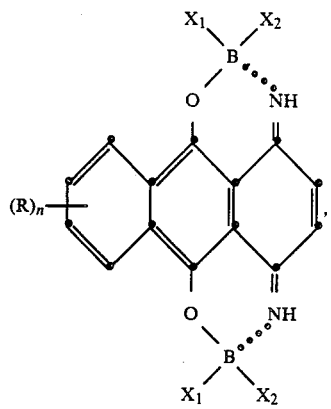

wherein $X_1$ and $X_2$ are halogen, R is alkyl, alkoxy, —$CO_2$alkyl, —CONHalkyl, —$SO_3M$ or —$CO_2M$, wherein M is hydrogen, ammonium or an alkali metal atom, nitro, cyano or halogen, and n is 0, 1 or 2.

2. A compound according to claim 1, wherein $X_1$ and $X_2$ are halogen and n is 0.

3. A process for the preparation of a compound as claimed in claim 1, which comprises reacting a corresponding 1,4-diaminoanthraquinone with a boron trihalide, or with boron triacetate or boron trisulfate, in an aromatic organic solvent and in the temperature range from 120° to 170° C., and isolating the reaction product.

4. A process according to claim 3, which comprises reacting a 1,4-diaminoanthraquinone with a boron trihalide in o-dichlorobenzene in the temperature range from 130° to 150° C.

5. A process according to claim 4, which comprises using the boron trihalide in the form of the etherate.

* * * * *